United States Patent [19]
Farbood et al.

[11] Patent Number: 5,188,129
[45] Date of Patent: Feb. 23, 1993

[54] TRICYCLIC ETHER-SUBSTITUTED ACETIC ACID, TOBACCO FLAVORING USE THEREOF AND PROCESS FOR PREPARING SAME

[75] Inventors: Mohamad I. Farbood, Holmdel; James A. Morris, Howell; Arthur E. Downey, Linden, all of N.J.; Jacob Kiwala, Brooklyn, N.Y.

[73] Assignee: International Flavors & Fragrances Inc., New York, N.Y.

[21] Appl. No.: 759,992

[22] Filed: Sep. 13, 1991

Related U.S. Application Data

[63] Continuation-in-part of Ser. No. 519,439, May 4, 1990, which is a continuation-in-part of Ser. No. 399,826, Aug. 28, 1989, Pat. No. 4,970,163.

[51] Int. Cl.[5] .............................. A24B 15/30
[52] U.S. Cl. .................................. 131/276; 131/274; 523/100
[58] Field of Search ................ 131/274, 276; 523/100, 523/101

[56] References Cited

U.S. PATENT DOCUMENTS

| | | | |
|---|---|---|---|
| 4,617,945 | 10/1986 | Vos et al. | 131/274 |
| 4,798,799 | 1/1989 | Farbood et al. | 435/254 |
| 4,872,917 | 10/1989 | Howe et al. | 131/276 |
| 4,970,163 | 11/1990 | Farbood et al. | 435/255 |

Primary Examiner—Paul Prebilic
Attorney, Agent, or Firm—Arthur L. Liberman

[57] ABSTRACT

Described are smoking tobacco compositions comprising smoking tobacco and intimately admixed therewith an aroma or taste augmenting, enhancing or imparting quantity of a tricyclic ether-substituted acetic acid having the structure:

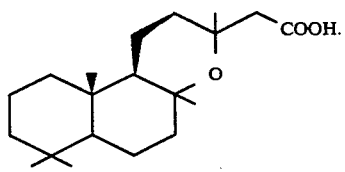

3 Claims, 7 Drawing Sheets

GC-MS SPECTRUM FOR EXAMPLE II (A).

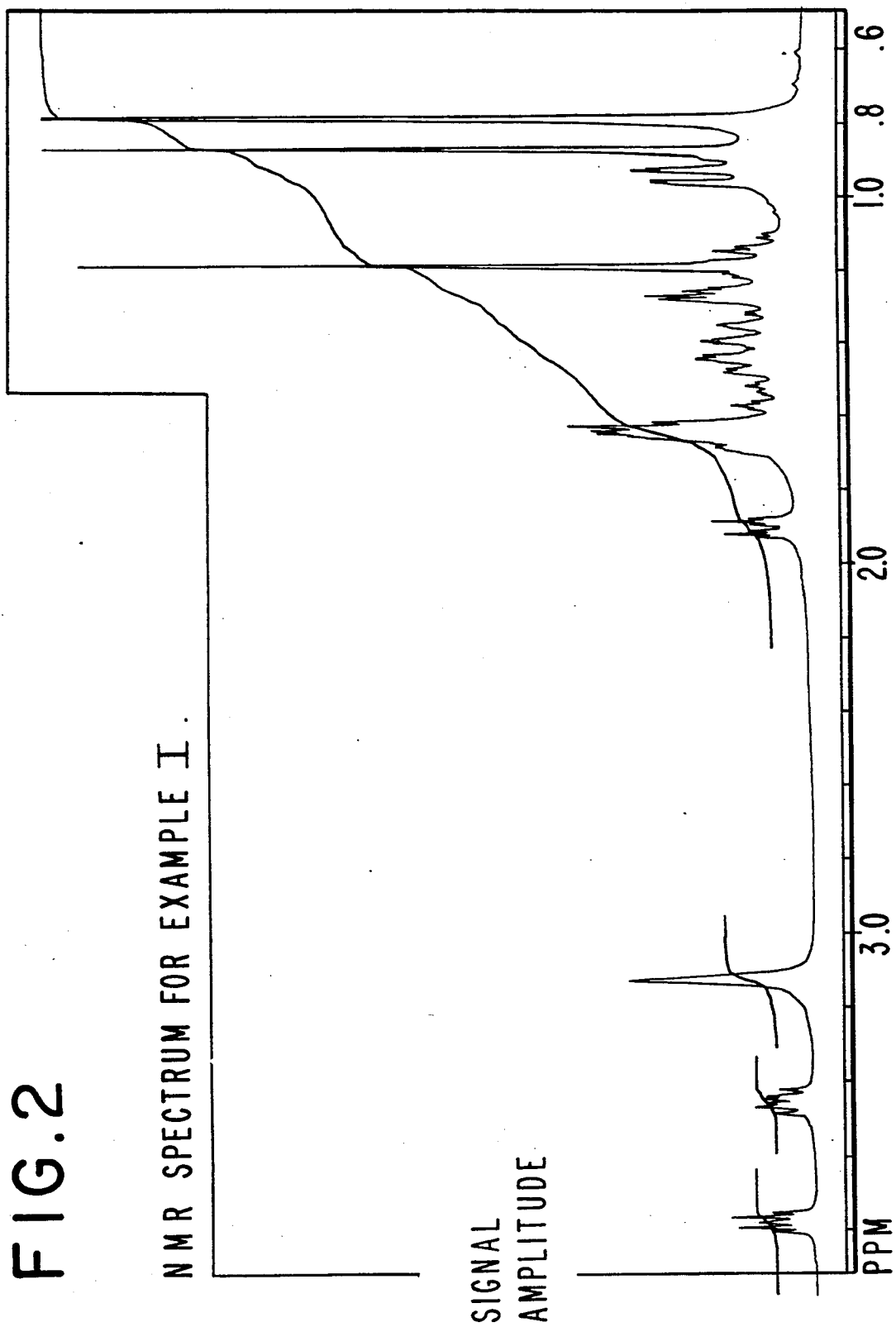
FIG. 2  NMR SPECTRUM FOR EXAMPLE I.

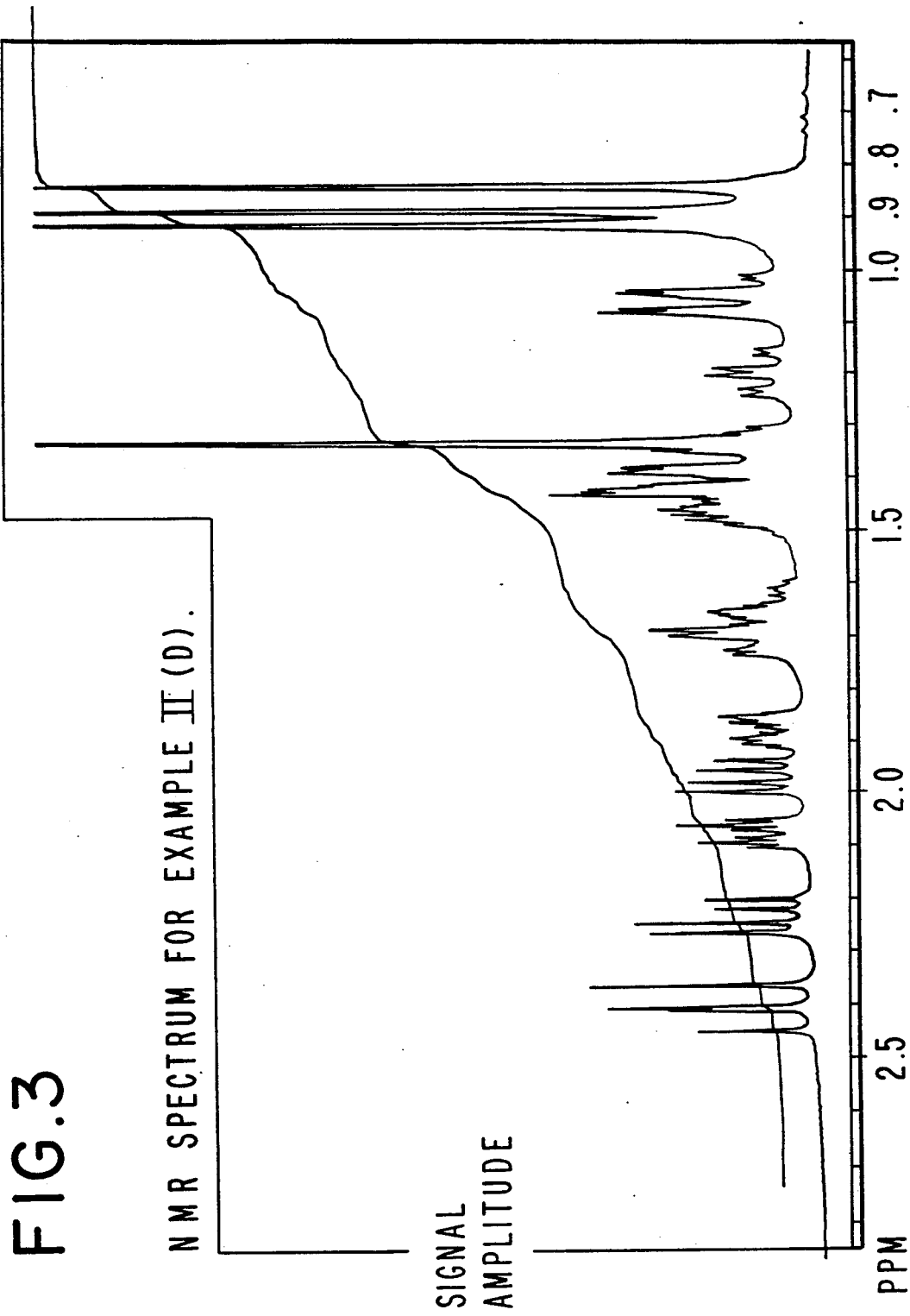

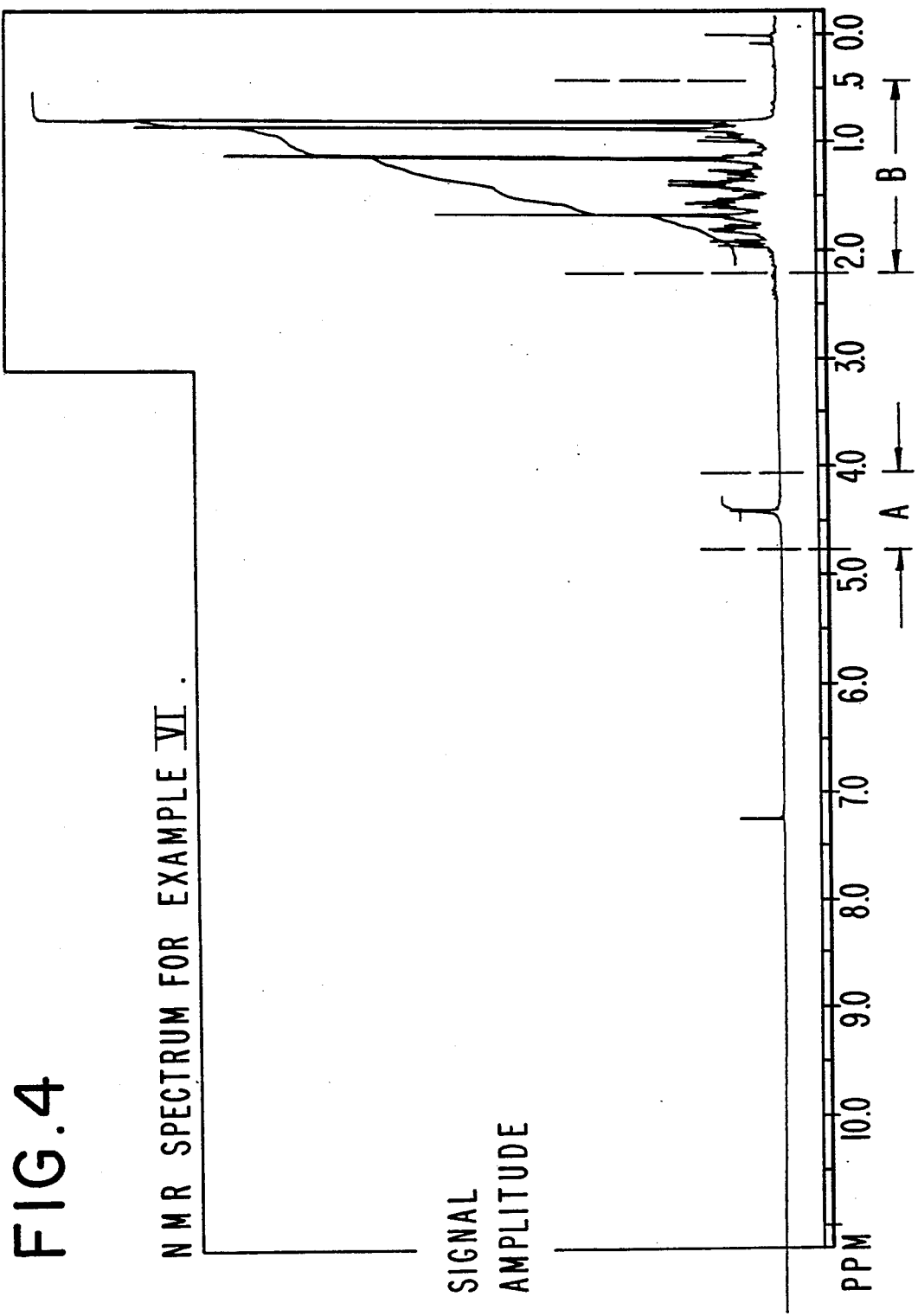
FIG. 4 NMR SPECTRUM FOR EXAMPLE VI

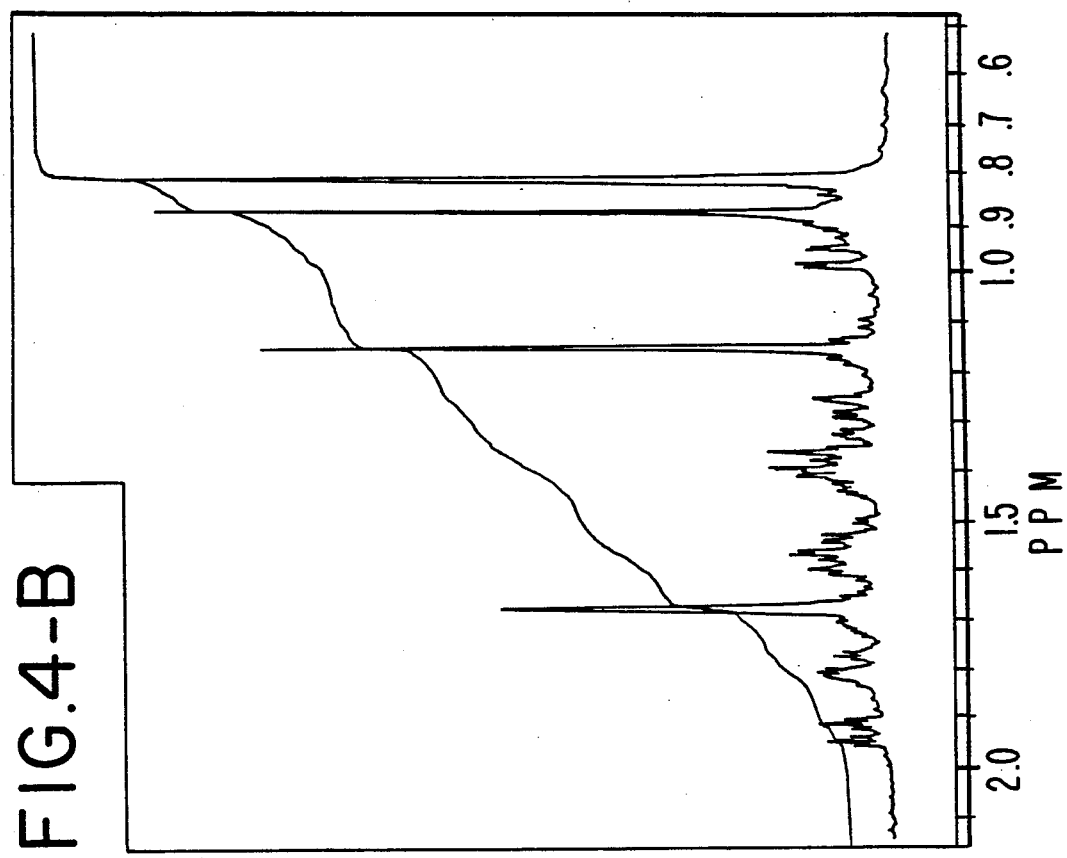
FIG.4-B
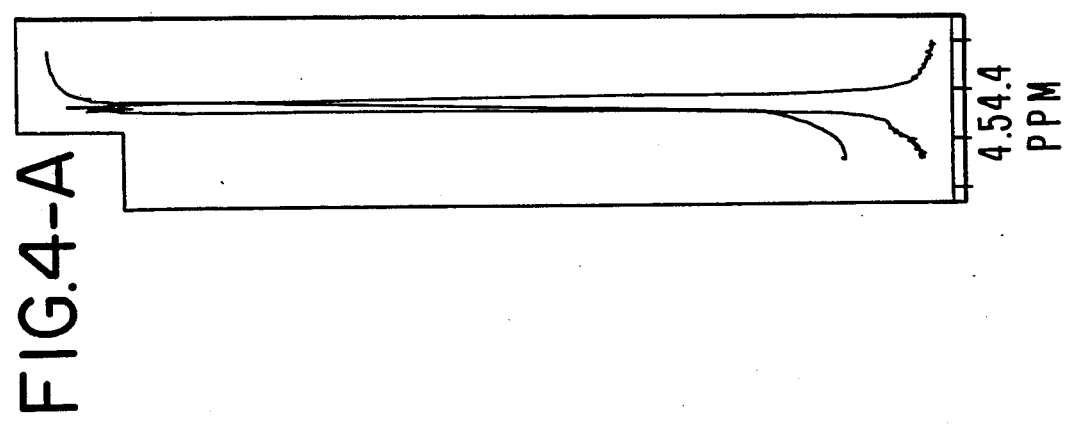
FIG.4-A

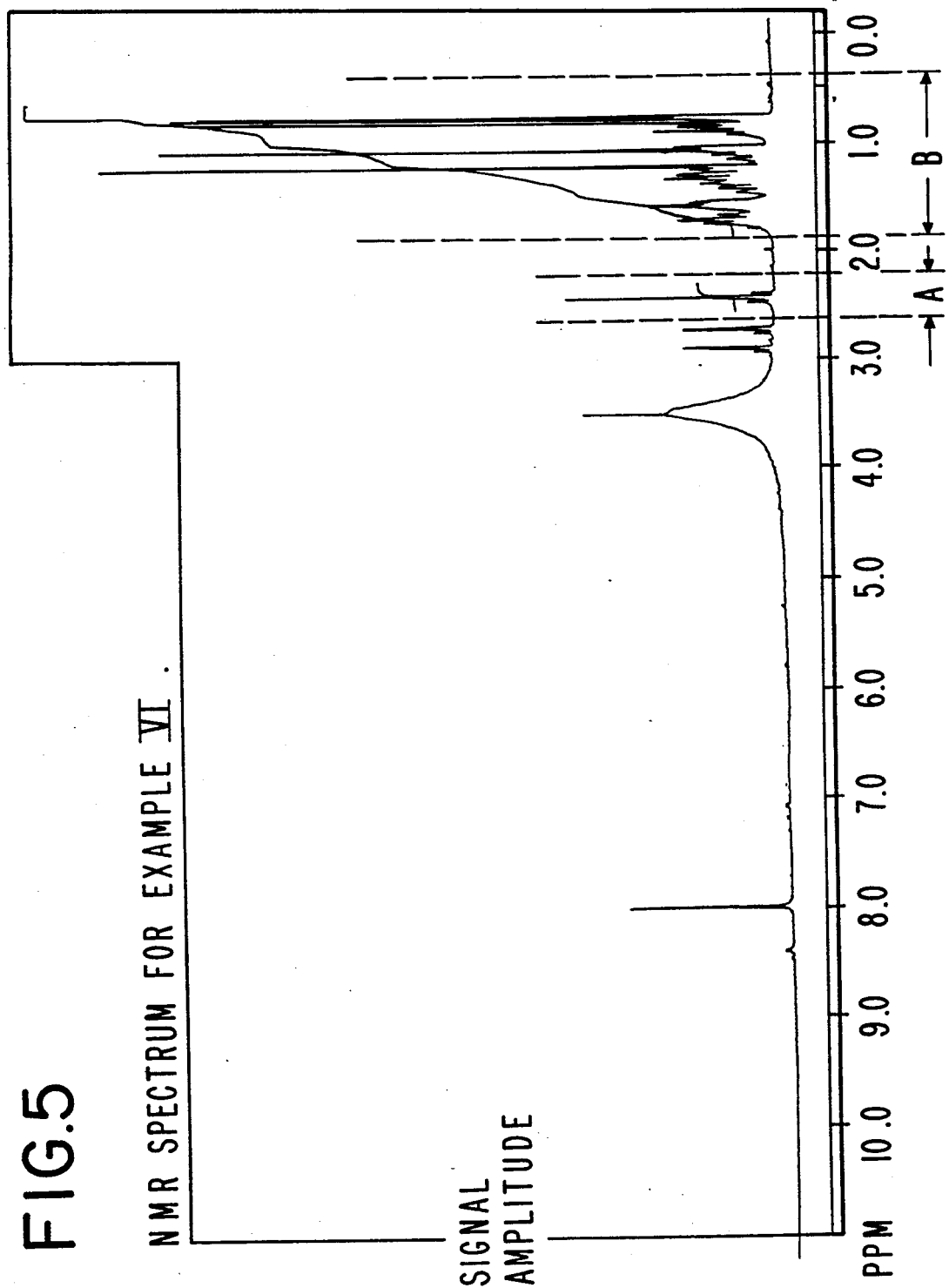

FIG.5-A
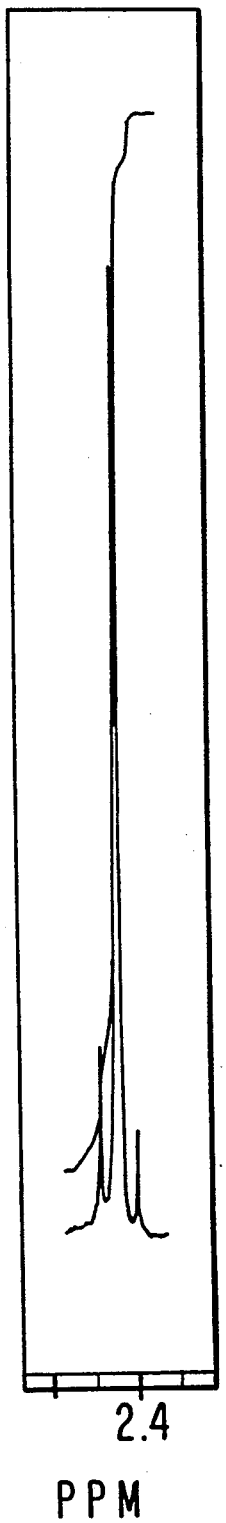
PPM
FIG.5-B
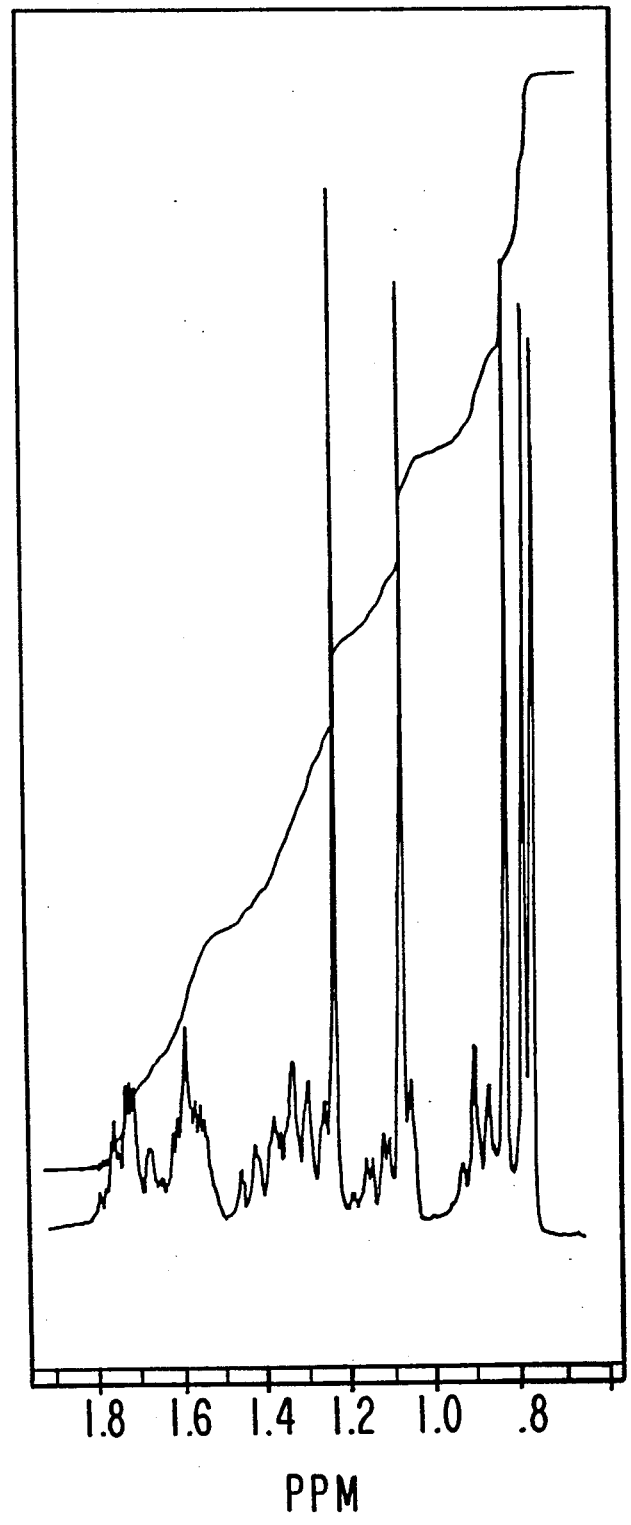
PPM

5,188,129

TRICYCLIC ETHER-SUBSTITUTED ACETIC ACID, TOBACCO FLAVORING USE THEREOF AND PROCESS FOR PREPARING SAME

PRIOR-FILED RELATED PATENT APPLICATIONS

This application is a continuation-in-part of application for U.S. patent Ser. No. 519,439 filed on May 4, 1990, which, in turn, is a continuation-in-part of application for U.S. patent Ser. No. 399,826 filed on Aug. 28, 1989, now U.S. Pat. No. 4,970,163 issued on Nov. 13, 1990.

BACKGROUND OF THE INVENTION

Our invention relates to the tricyclic ether-substituted acetic acid having the structure:

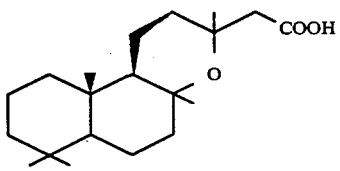

and microbiological processes for producing same from one or both of the compounds having the structures:

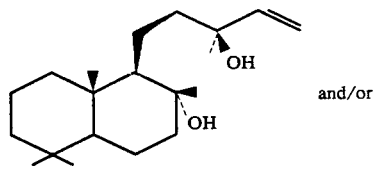

and/or

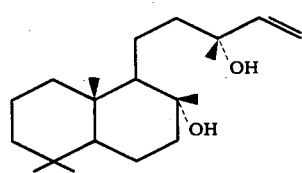

as a substrate and using one of the microorganisms:
 Cryptococcus albidus, ATCC 20918
 Bensingtonia ciliata, ATCC 20919
 Cryptococcus laurentii, ATCC 20920 or
 Cryptococcus albidus, ATCC 20921.

Also described is the use of the tricyclic ether-substituted acetic acid having the structure:

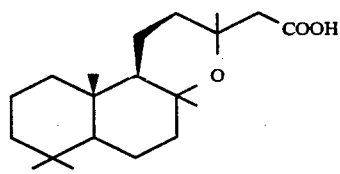

is augmenting, enhancing or imparting an aroma or taste in or to a smoking tobacco article or smoking tobacco by causing the tobacco to be richer, smoother, and have more "tobacco body".

The tricyclic ether-substituted acetic acid having the structure:

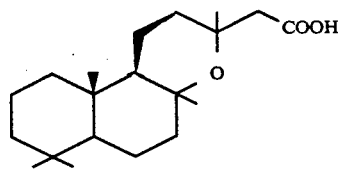

along with the cyclic ether having the structure:

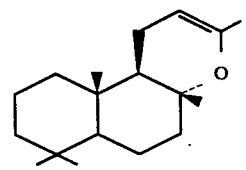

were discovered to be produced in carrying out the fermentation process commencing with sclareol having the structures:

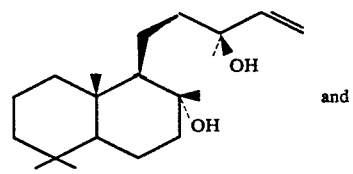

and

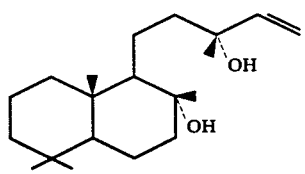

in an effort to produce sclareolide having the structure

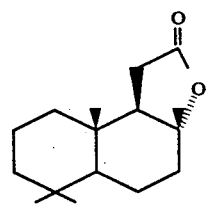

The pathway from sclareolyde to sclareolide was originally determined to be:

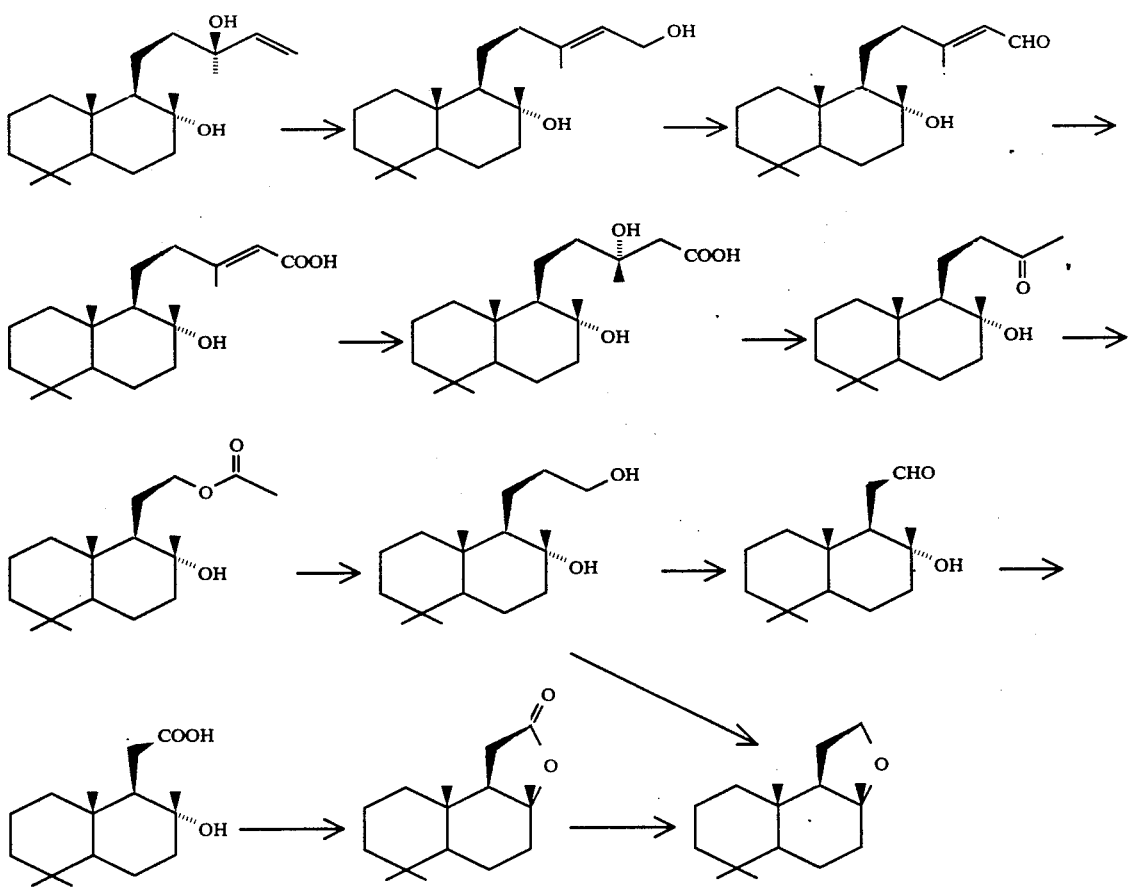

with the ultimate end product being the compound having the structure:

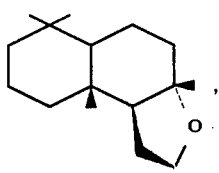

an important material for use in perfumery.

The compound having the structure:

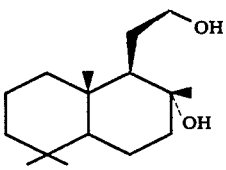

has been shown to be useful in U.S. Pat. No. 4,798,799 issued Jan. 17, 1989 as an intermediate in the creation of the compound having the structure:

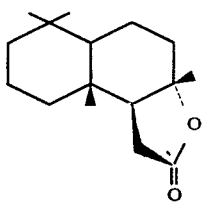

and has also been shown to be a useful precursor of the compound having the structure:

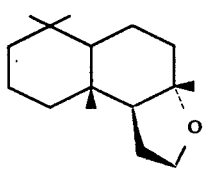

at column 8, lines 58-60 of U.S. Pat. No. 4,798,799.

Indeed, U.S. Pat. No. 4,798,799 discloses the utilization of a culture containing the microorganism *Hyphozyma roseoniger* having the identifying characteristics of CBS 214.83 and ATCC 20624 capable of producing the diol having the structure:

in a recoverable quantity upon the transformation of compounds including the compound having the structure:

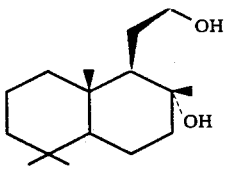

(sclareol). Table IV, thereof at column 12, lines 15–28 discloses yields of 96% when carrying out the reaction:

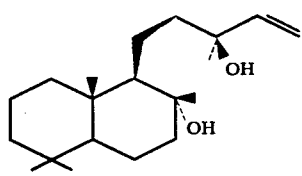

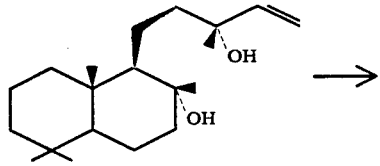

under fermentation conditions using ATCC 20624.

There is no teaching or suggestion in the prior art of producing during the foregoing reaction sequences the tricyclic ether-substituted acetic acid having the structure:

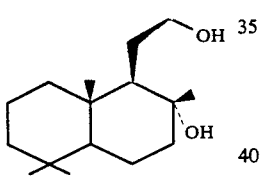

Materials which are capable of causing tobacco to be richer, smoother and have more body; particularly, for the purposes of imparting, augmenting or enhancing aroma and taste in "low delivery" cigarettes where the smoke is thinner are highly desirable in the smoking tobacco art. Many of the natural materials which provide such aroma and taste nuances are high in cost, unobtainable at times, vary in quality from one batch to another and/or are generally subject to the usual variations of natural products.

The tricyclic ether-substituted acetic acid having the structure:

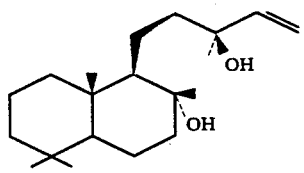

can be classified as a "natural product" in view of the process used in preparing it from natural sclareol having one or both of the structures:

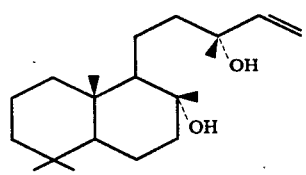 and/or

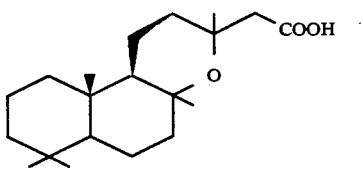

Nothing in the prior art discloses the compound having the structure:

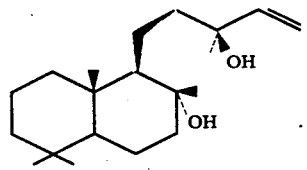

or its use in smoking tobacco articles or smoking tobacco per se.

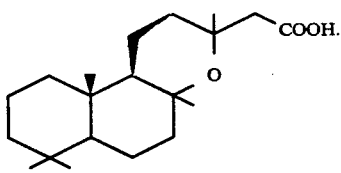

Figure 1:
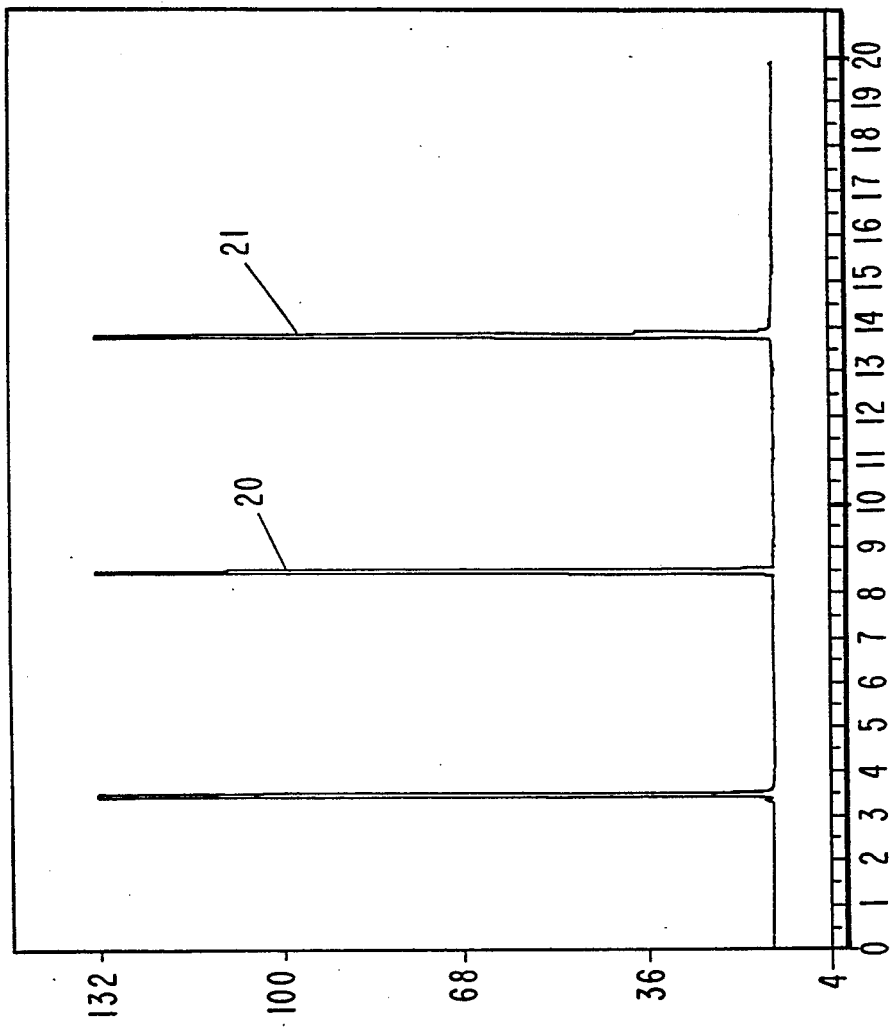
FIG. 1 is a GC-MS spectrum for the starting material of Example III. The peak indicated by reference numeral 21 is the peak for sclareol having the structure.

The peak indicated by reference numeral 20 is the peak for the internal standard, the compound having the structure:

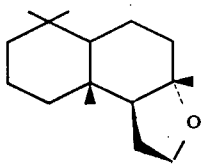

FIG. 2 is the NMR spectrum for the reaction product of Example II, the compound having the structure:

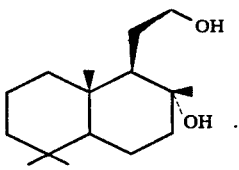

FIG. 3 is the NMR spectrum for the reaction product of Example III having the structure:

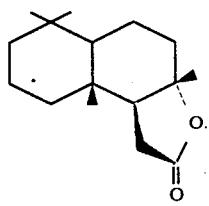

FIG. 4 is the NMR spectrum for the compound having the structure:

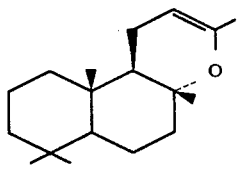

produced according to Example VI.

FIG. 4A is a detailed section "A" of the NMR spectrum of FIG. 5.

FIG. 4B is a detailed section "B" of the NMR spectrum of FIG. 5.

FIG. 5 is the NMR spectrum of the compound having the structure:

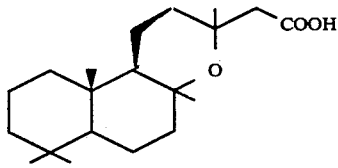

produced according to Example VI.

FIG. 5A is a detailed section "A" of the NMR spectrum of FIG. 5.

FIG. 5B is a detailed section "B" of the NMR spectrum of FIG. 5.

SUMMARY OF THE INVENTION

The present invention concerns the tricyclic ether-substituted acetic acid having the structure:

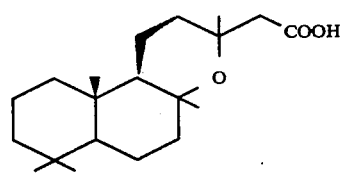

prepared according to the reaction:

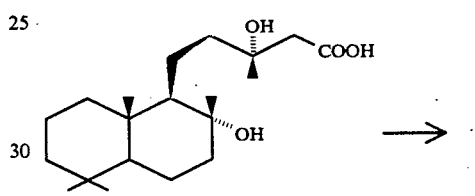

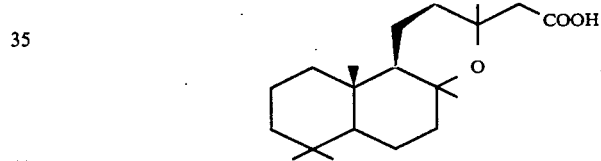

The compound having the structure:

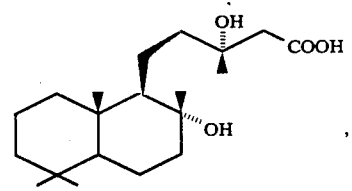

the precursor of the tricyclic ether-substituted acetic acid having the structure:

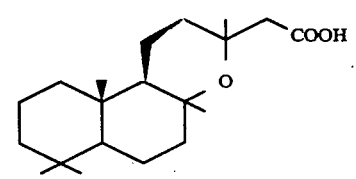

is one of the intermediate in the pathway for transformation of sclareol to scalareolide by *Cryptococcus albidus* which pathway is as follows:

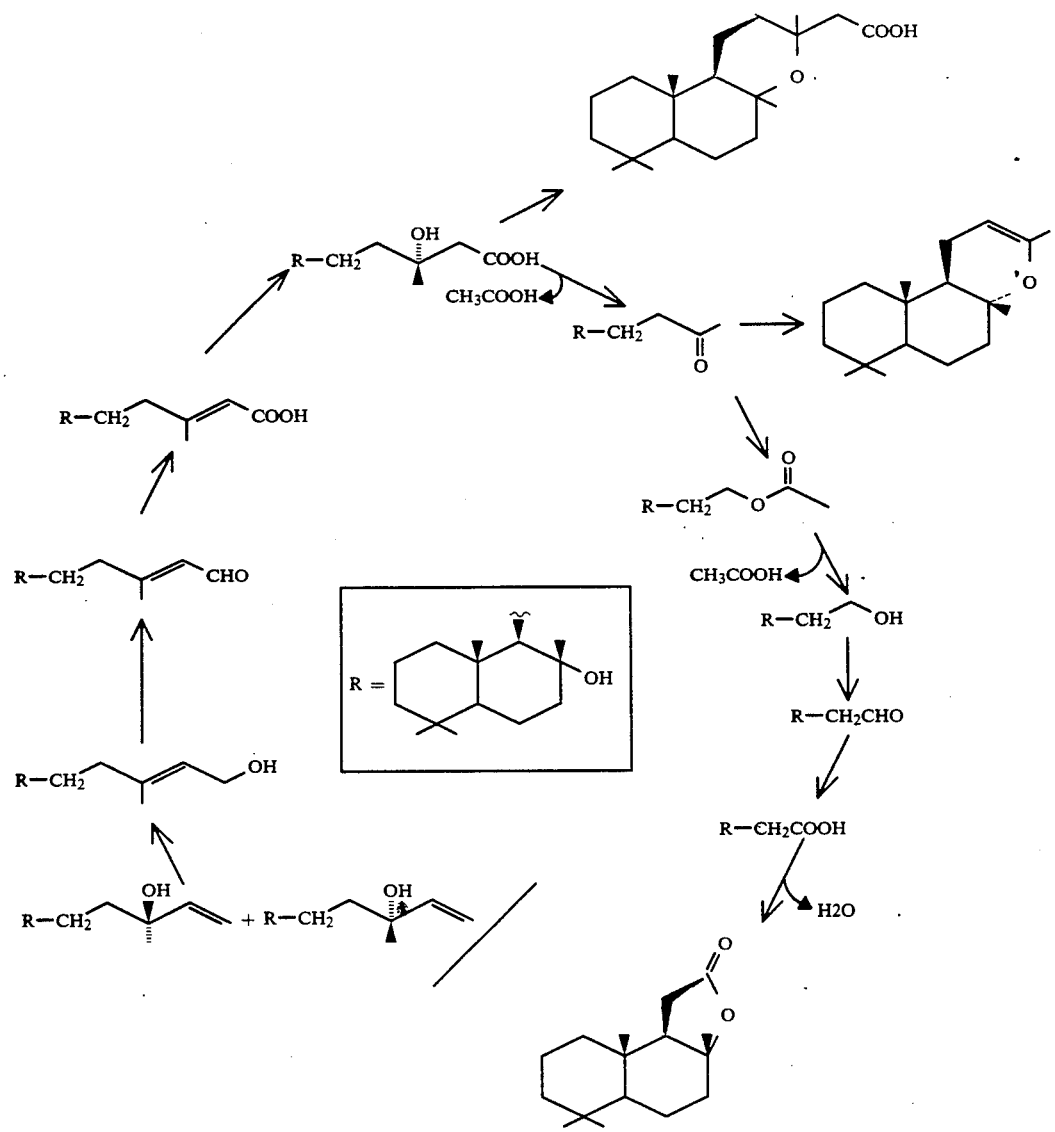
Heretofore, the compound having the structure:
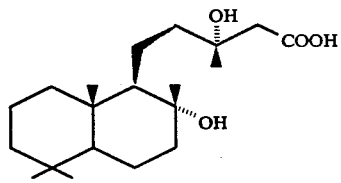
in the above pathway was not known to be capable of producing the tricyclic ether-substituted acetic acid having the structure:
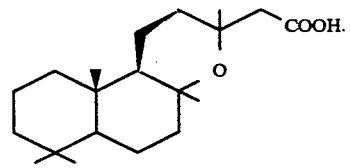
The compound having the structure:
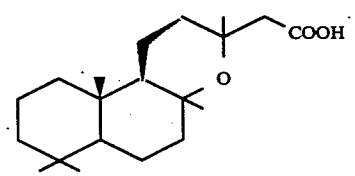
can also be shown to be produced in the foregoing pathway, thusly:

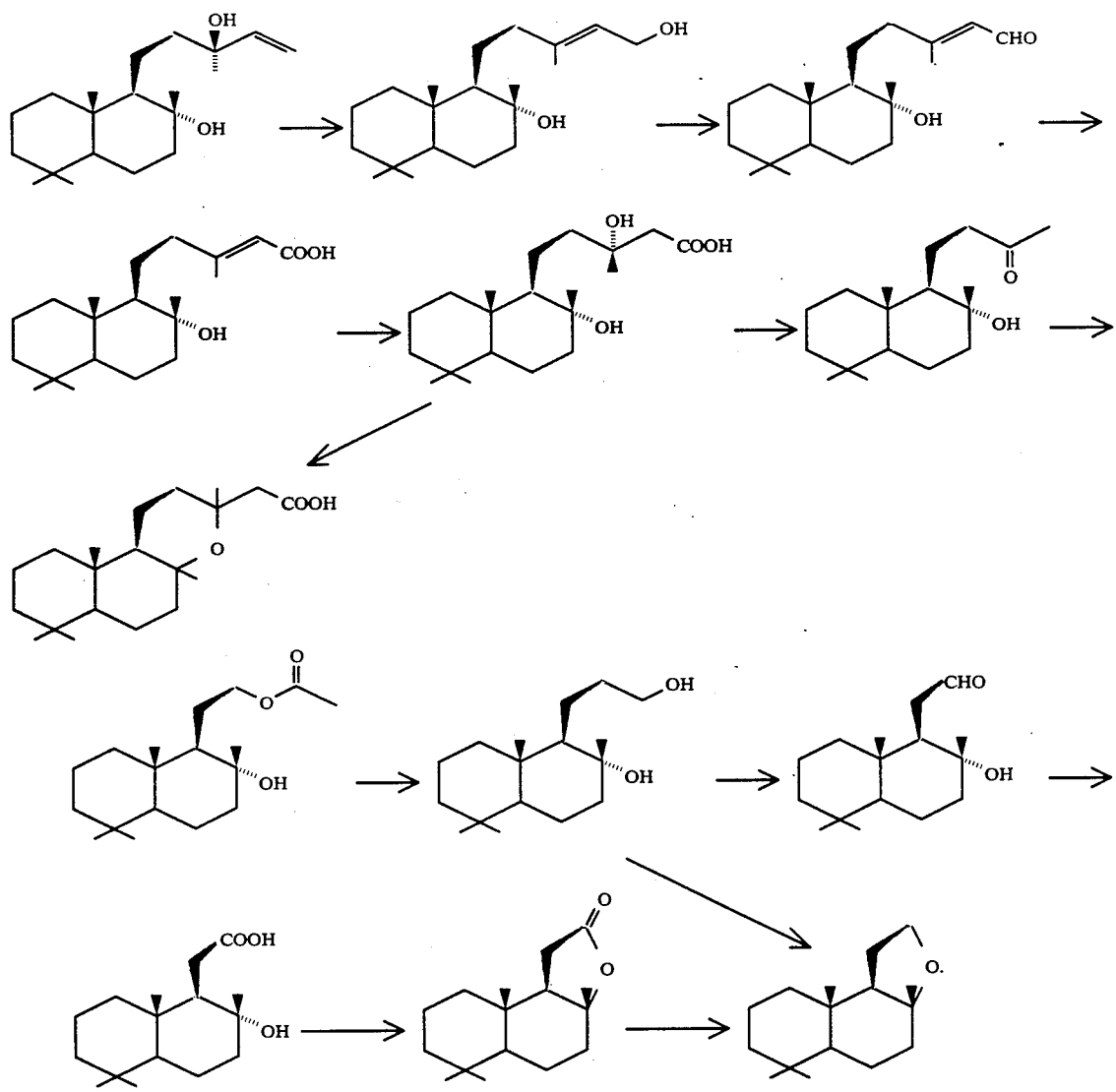
The compound having the structure:
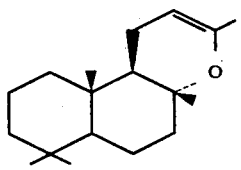
is produced to the reaction:
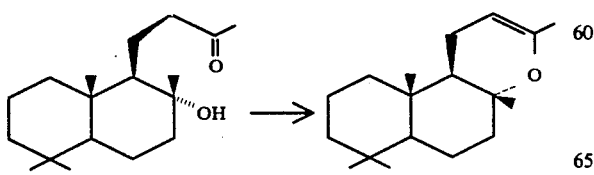
from another intermediate in the above pathway having the structure:
The compound having the structure:
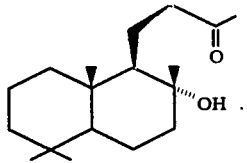
is produced subsequent to filtration of the sclareolide having the structure:
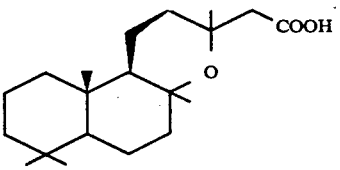

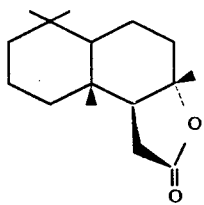

by means of acidification of the fermentation broth at a pH of 2 followed by further crystallization and subsequent chromatographic separation of the resulting products. One of the products evolved as a result of the chromatographic separation is the compound having the structure:

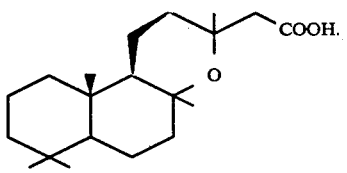

The compound having the structure:

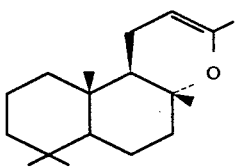

is obtained during the crystallization of the sclareolide having the structure:

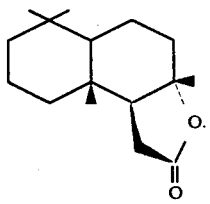

When the sclareolide having the structure:

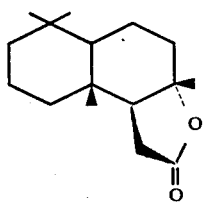

is purified by crystallization, the supernatant liquid is concentrated to 25-30% of its volume and chromatographically separated. The first fraction eluted from the chromatographic column is the compound having the structure:

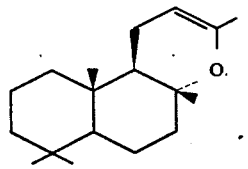

Thus, in general, the present invention concerns biologically pure cultures of the microorganisms:
Cryptococcus albidus, ATCC 20918;
Bensingtonia ciliata, ATCC 20919;
Cryptococcus laurentii, ATCC 20920; and
Cryptococcus albidus, ATCC 20921.

In another embodiment the present invention concerns cultures containing the microorganisms:
Cryptococcus albidus, ATCC 20918;
Bensingtonia ciliata, ATCC 20919;
Cryptococcus laurentii, ATCC 20920; and
Cryptococcus albidus, ATCC 20921,
said cultures individually capable of producing either the diol having the structure:

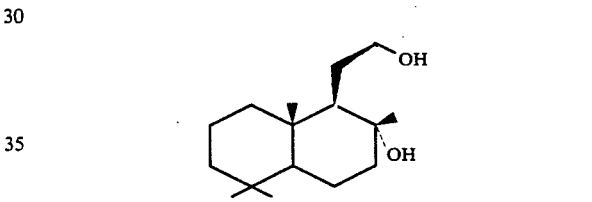

or sclareolide having the structure:

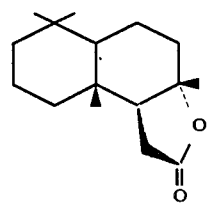

as follows:
Cryptococcus albidus, ATCC 20918 and
Cryptococcus albidus, ATCC 20921,
capable of producing sclareolide having the structure:

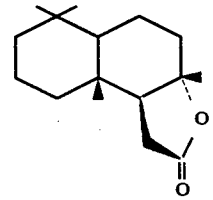

from a mixture of sclareol having the structure:

15

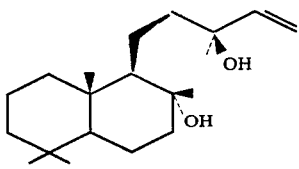

and episclareol having the structure:

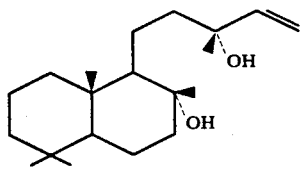

*Bensingtonia ciliata*, ATCC 20919 and *Cryptococcus laurentii*, ATCC 20920 capable of producing the diol having the structure:

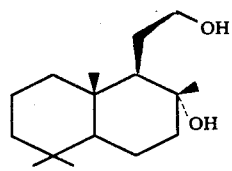

from the mixture or sclareol having the structure:

16

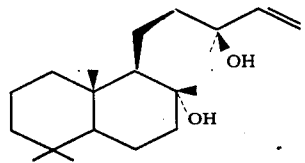

and episclareol having the structure:

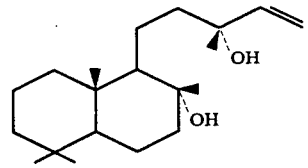

under aerobic conditions in an aqueous nutrient medium.

In still another embodiment the present invention concerns mixtures prepared by cultivating the microorganisms (individually) as follows:

*Cryptococcus albidus* having the identifying characteristics of ATCC 20918;

*Bensingtonia ciliata* having the identifying characteristics of ATCC 20919;

*Cryptococcus laurentii* having the identifying characteristics of ATCC 20920; and

*Cryptococcus albidus* having the identifying characteristics of ATCC 20921 under aerobic conditions in an aqueous nutrient medium.

Thus, in carrying out the reaction using:

*Cryptococcus albidus*, ATCC 20918 or
*Cryptococcus albidus*, ATCC 20921 the following pathway exists:

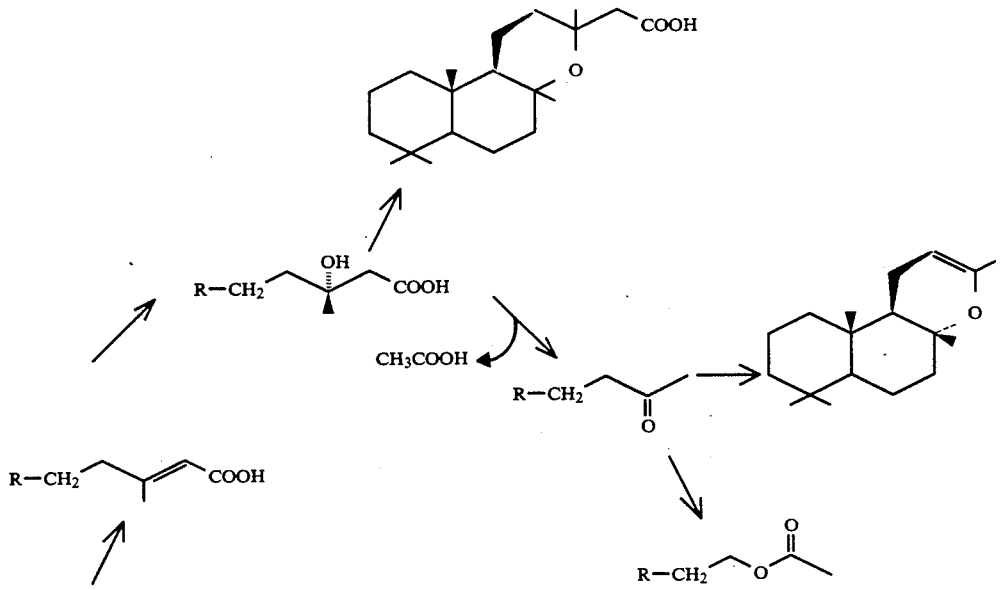

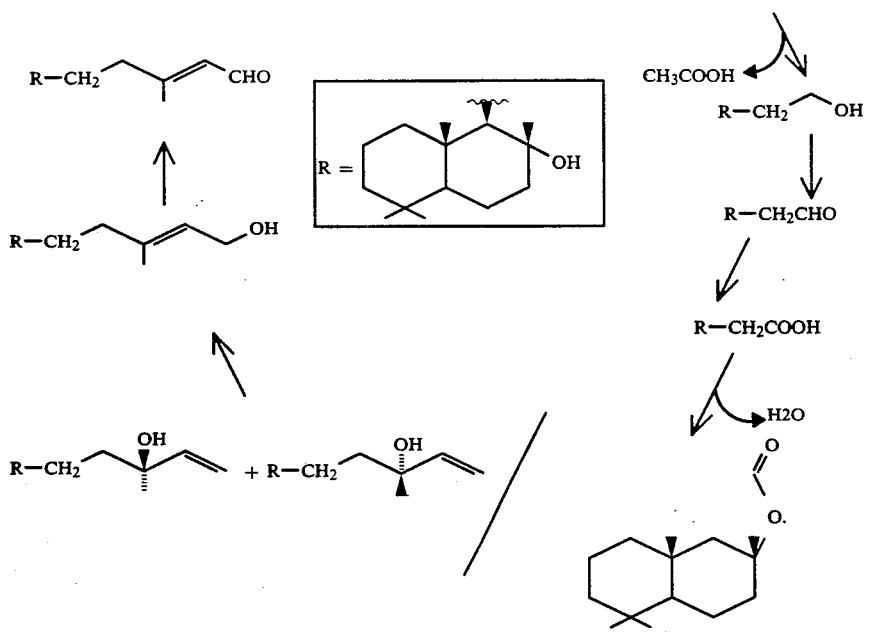
This pathway can be rewritten, thusly:
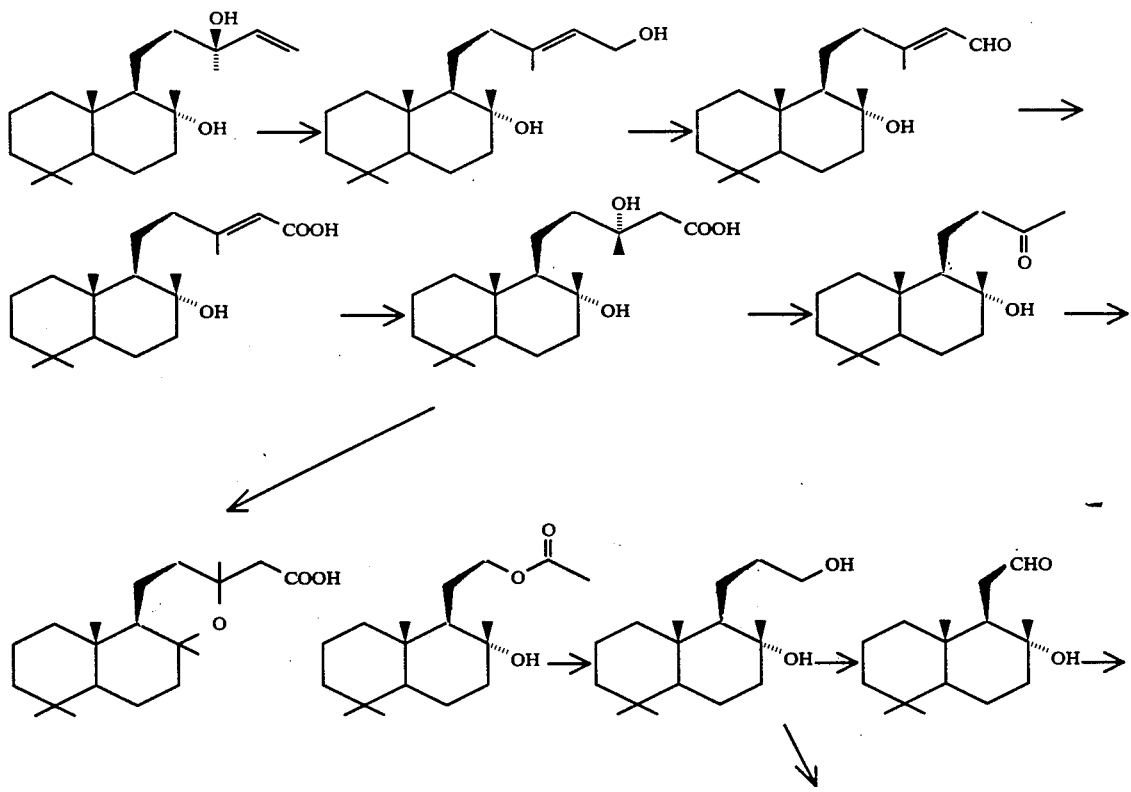

-continued

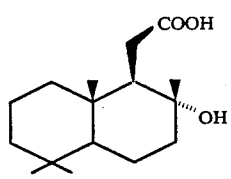 → 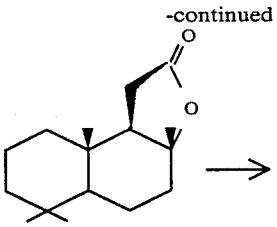 → 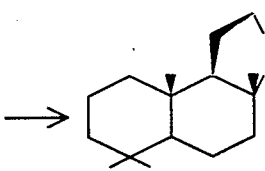

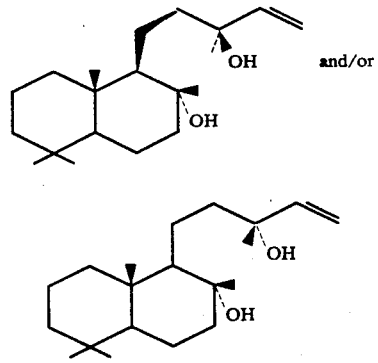

The form in which the microorganisms are used is not critical. They can be used as the culture (suspension), i.e., including the cells and the corresponding nutrient solution, or in the form of cells suspended in a buffer solution. The cells, or an enzyme extract thereof, may be immobilized on a suitable solid support, which may then be used to effect transformations.

The suspended culture mixture is prepared by inoculation of a suitable aqueous nutrient medium with the microorganisms. A suitable nutrient medium is one which contains nitrogen sources, inorganic salts, growth factors, the desired substrate(s), and optionally other carbon sources. Some carbon sources suitable for use in the inventive process include, for example, glucose, galactose, L-sorbose, maltose, sucrose, cellobiose, trehalose, L-arabinose, L-rhamnose, ethanol, glycerol, L-erythrithol, D-mannitol, lactose, melibiose, raffinose, melezitose, starch, D-xylose, D-sorbitol, a-methyl-D-glucoside, lactic acid, citric acid and succinic acid. Suitable nitrogen sources include, for example, nitrogen-containing organic substances such as peptone, meat extract, yeast extract, corn steep liquor, casein, urea, amino acids, or nitrogen-containing inorganic compounds such as nitrates, nitrites and inorganic ammonium salts. Suitable inorganic salts include, for example, phosphates of magnesium, potassium, calcium, or sodium. The above mentioned culture medium nutrients may be supplemented with, for example, one or more vitamins of the B group and/or one or more trace minerals such as Fe, Mo, Cu, Mn, and B, as desired. The vitamins or trace minerals are not necessary when a small amount of yeast extract is added to the medium. Addition of an antibiotic, such as chloroamphenicol or chlorotetracycline, may be desirable when bacterial contamination is a problem.

The cultivation of the microorganism may be carried out as a stationary culture or as a submerged (e.g., shaking culture, fermentor culture) under aerobic conditions. One may suitably work in the pH range of from about 2.5 to about 9.0, and preferably in the range of from about 3.0 to about 7.5 and most preferably between about 3.0 and 6.5. The pH may be regulated by the addition of inorganic or organic acids, such as hydrochloric acid, acetic acid, and oxalic acid, or by the addition of bases, such as sodium hydroxide, and ammonium hydroxide, or by the addition of a buffer, such as phosphate or phthalate. The incubation temperature should suitably be maintained between about 12° C. and about 33° C., with a range between about 15° C. and about 30° C. being more preferred, and a range between about 18° C. and about 28° C. being most preferred.

The process in accordance with this invention may be conveniently carried out by adding one or a mixture of the compounds having the structures:

to the nutrient medium at the onset of cultivation, as the sole carbon source. Alternatively, the substrate may be added in combination with another carbon source, such as dextrose, either during cultivation, or when the carbon source is depleted. The only restriction on the concentration of substrate in the culture medium is that of being able to effectively aerate the culture. However, the substrate concentration is preferably in the range of between about 0.1 g/L and about 130 g/L, more preferably in the range of between about 0.5 g/L and about 120 g/L, and most preferably in the range between about 2.5 g/L up to about 100 g/L. The transformation can be suitably carried out under any of the above mentioned conditions.

The total transformation time (after initial cultivation period) may vary depending on the composition of the nutrient medium and the substrate concentration. In general, shaking flask cultures require from between about 12 hours and about 264 hours. However, when a fermentor is used the cultivation time may be reduced to about 48 hours or less.

The transformation may be carried out using the cells of the microorganism isolated from the culture solution, or with an enzyme extract isolated from the cells in a manner well known to the art. In this case, the transformation can be conveniently carried out in a variety of aqueous nutrient media including, for example, in a buffer solution, in a physiological salt solution, in a fresh nutrient solution, or in water. The isolated cells or enzyme extract may be immobilized on a solid support and the desired transformation effected. Also, transformation of the substrate may be effected by mutants of this organism. Such mutants can be readily obtained by methods well known in the art, for example, by exposing the cells to UV or X-rays, or known mutagenic substances, such as, for example, acridine orange.

The substrate can be added to the medium as a powder, or a slurry in an emulsifier such as TWEEN ® 80 (polyoxyethylenesorbitan mono-oleate), or as a solution in an emulsifier, or as a solution in a hydrophilic solvent such as acetone, methanol, ethanol, ethylene glycol, or dioxan. A surface-active agent, or a dispersion agent can also be added to an aqueous suspension of the substrate, or the substrate can be emulsified using ultrasound.

Conventional antifoam agents, such as silicone oils (e.g., UCON), polyalkyleneglycol derivatives, maize oil, or soya oil, can be used to control foaming.

The transformation of the substrate can be monitored using standard analytical techniques such as GLC, TLC, HPLC, IR and NMR. If a rapid disappearance of the substrate is observed more substrate can then be added, in order to maximize the transformation capacity of the microorganism. The process is generally terminated when most of the substrate has disappeared from the culture medium. Depending upon the microorganism used, the compound having the structure:

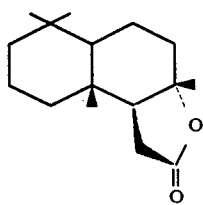

or the compound having the structure:

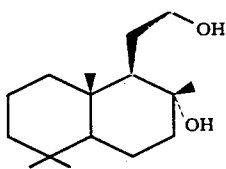

may be recovered from the aqueous nutrient medium. The compound having the structure:

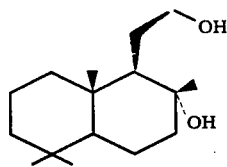

may be cyclized to the compound having the structure:

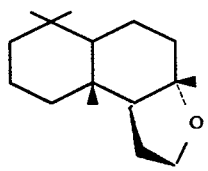

as stated at lines 52 and 53, at column 8 of U.S. Pat. No. 4,798,799 the specification for which is incorporated by reference herein. The compound having the structure:

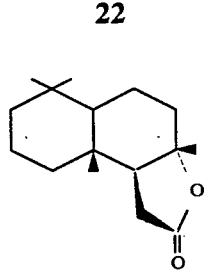

may also be used as is for its flavor or fragrance value or it may be reduced to the compound having the structure:

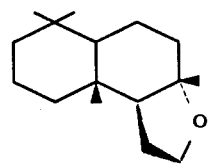

according to the reaction:

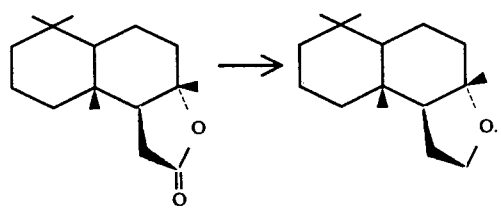

As stated, supra, and as shown in the foregoing pathways the tricyclic ether-substituted acetic acid of our invention may be prepared according to the reaction:

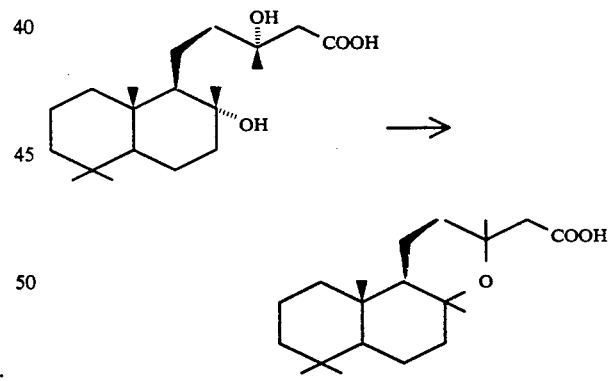

when carrying out the acidification of the fermentation broth subsequent to the filtration of the compound having the structure:

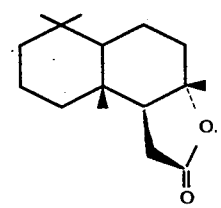

This is shown in more detail in Example VI, infra.

An aspect of our invention provides an organoleptically improved smoking tobacco product and additive therefor including methods of making the same which overcome problems heretofore encountered in the creation or enhancement of specific desired rich, smooth, high body tobacco nuances on smoking in the main stream and in the side stream. Such notes both prior to and on smoking both in the main stream and in the side stream may now be readily controlled and maintained at the desired uniform level regardless of variations in the tobacco components of the blend; or the nature of the filter used in conjunction with the smoking tobacco article.

This invention further provides improved tobacco additives and additives for materials used in fabrication of tobacco articles (particularly smoking tobacco articles) and methods whereby desirable rich, smooth, "high body" tobacco nuances on smoking may be imparted to smoking tobacco compositions and smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient the tricyclic ether-substituted acetic acid of our invention having the structure:

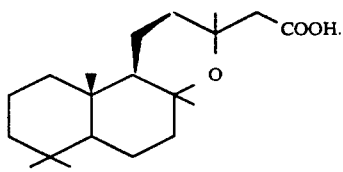

In addition to the tricyclic ether-substituted acetic acid of our invention having the structure:

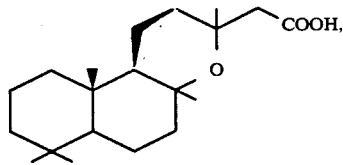

other flavoring and aroma additives may be added to the smoking tobacco material or substitute therefor either separately or in admixture with the tricyclic ether-substituted acetic acid of our invention, thusly:

I. Synthetic Materials

Beta-methylcinnamaldehyde;
Eugenol;
Dipentene;
Damascenone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1,3-nonadiene-8-one;
2-Methyl -5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphthol(2,1-beta-furan);
4-Hydroxyhexenoic acid, gamma-lactone;
Polyisoprenoid hydrocarbons defined in Example V of U.S. Pat. No. 3,589,372 issued on Jun. 29, 1971.

II. Natural Oils

Celery seed oil;
Coffee extract;
Bergamot oil;
Cocoa extract;
Nutmeg oil; and
Origanum oil.

An aroma and flavoring concentrate containing the tricyclic ether-substituted acetic acid of our invention having the structure:

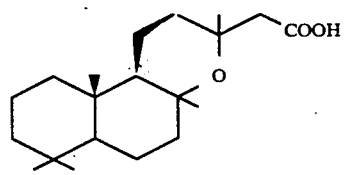

and, if desired, one or more of the above indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of rich, smooth, "high body" tobacco nuances prior to and on smoking in both the main stream and the side stream, we have found that satisfactory results are obtained particularly in "low delivery" smoking articles, e.g., cigarettes if the proportion by weight of the tricyclic ether-substituted acetic acid having the structure:

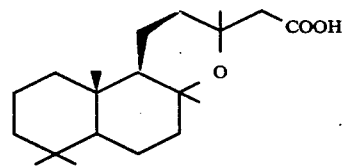

to smoking tobacco material is between 50 ppm and 2500 ppm (0.005%–0.25%) of the active ingredients to the smoking tobacco material. We have further found that satisfactory results are obtained if the proportion by weight of the tricyclic ether-substituted acetic acid having the structure:

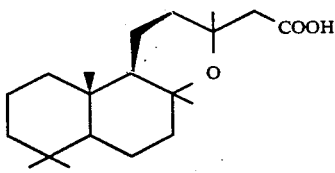

to flavoring material is between 0.05:1 and 0.50:1. We have further found that satisfactory results are obtained if the proportion by weight of the tricyclic ether-substituted acetic acid having the structure:

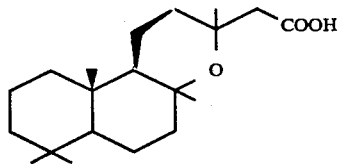

to smoking tobacco material containing other active ingredients is between about 20 ppm and about 40 ppm, preferably 25 ppm.

Any convenient method for incorporating the tricyclic ether-substituted acetic acid of our invention the tobacco product may be employed. Thus, the tricyclic ether-substituted acetic acid of our invention having the structure:

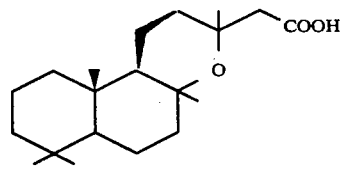

taken alone or along with other flavoring additives may be dissolved in a suitable solvent such as food grade ethanol, pentane, diethyl ether and/or other volatile organic solvents and the resulting solution may either be sprayed on the cured, cased and blended tobacco material; or the tobacco material or filter may be dipped into such solution. Under certain circumstances, a solution of the tricyclic ether-substituted acetic acid of our invention having the structure:

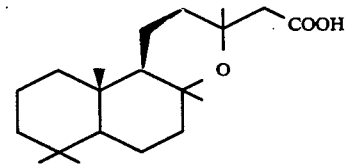

taken alone or taken further together with other flavoring additives as set forth above may be applied by means of a suitable applicator such as a brush or roller on the paper or leaf wrapper for the smoking product or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the tricyclic ether-substituted acetic acid of our invention having the structure:

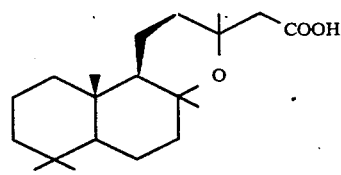

in excess of the amounts or concentrations indicated above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco, dust or fines may also be used. As stated, supra, the tricyclic ether-substituted acetic acid of our invention having the structure:

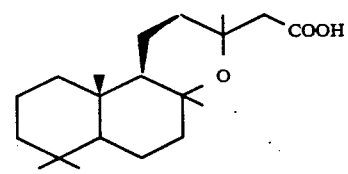

can be incorporated with material such as filter tip materials, seam paste, packaging materials and the like which are used along with the tobacco to form a product adapted for smoking. Further, the tricyclic ether-substituted acetic acid of our invention having the structure:

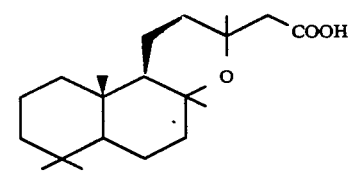

can be added to certain tobacco substitutes of natural or synthetic origin (e.g., dried lettuce leaves or mate't)(x Argentina or Paraguay) and, accordingly, by the term "tobacco" as used throughout this specification is meant any composition intended for human consumption by smoking or otherwise, whether composed of tobacco plant parts or substitute material or both.

It will thus be apparent that the tricyclic ether-substituted acetic acid of our invention having the structure:

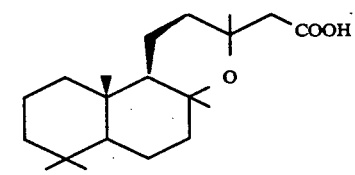

can be utilized to alter, modify, augment or enhance sensory properties, particularly organoleptic properties such as flavor and/or fragrances of smoking tobacco materials and articles.

The following Examples I–VI, inclusive, serve to illustrate processes for carrying out production of materials associated with and which contain the tricyclic ether-substituted acetic acid of our invention having the structure:

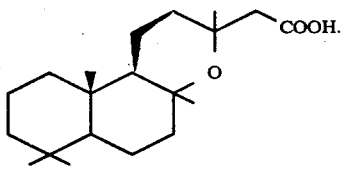

The following Example VII, et seq. sets forth the use of the product of Example VI of our invention. The invention is to be considered restricted to these examples only as indicated in the appended claims.

All parts and percentages given herein are by weight unless otherwise specified.

EXAMPLE I

Effect of pH on Conversion of Sclareol to Sclareolide Using *Cryptococcus albidus* (Saito [Skinner var. albidus]) (ATCC 20918)

Reactions

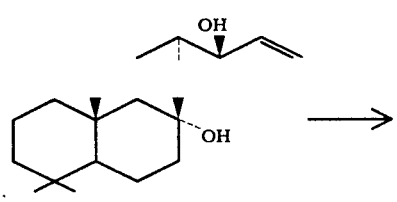

→

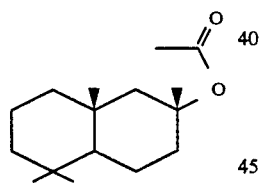

and

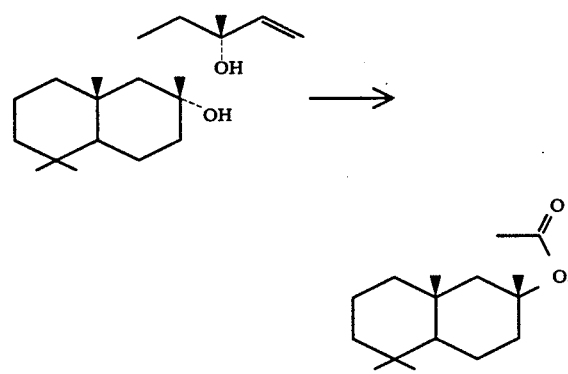

The following medium was prepared:

| | |
|---|---|
| NH$_4$NO$_3$ | 0.1% |
| KH$_2$PO$_4$ | 0.1% |
| MgSO$_4$.7H$_2$O | 0.05% |
| Yeast Extract | 0.2%. |

Eleven 500 ml flasks each containing 100 ml of medium and 1 g of sclareol in TWEEN® 80 (ratio of sclareol of TWEEN® 80=2:1).

Each flask was inoculated with 5 ml of a 24 hour culture grown on dextrose at 25° C. and 150 rpm. Product and substrate were monitored by TLC against a known standard.

The "substrate" is sclareol which is an 80:20 mixture of the compound having the structure:

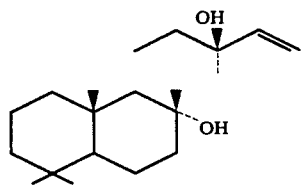

and the compound having the structure:

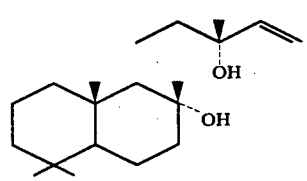

the "Intermediate" is the compound having the structure:

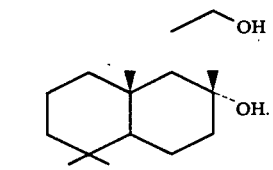

The "product" is sclareolide, the compound having the structure:

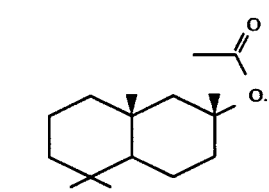

TABLE I

| Flask No. | pH | 24 Hours | 48 Hours | 72 Hours |
|---|---|---|---|---|
| 1 | 2.5 | TP + S + TI | P + S + I | P + S + TI |
| 2 | 3.0 | P + TS + I | P + S + I | P |
| 3 | 3.5 | P + TS + TI | P + TI | P |
| 4 | 4.0 | P + TS + I | P + TI | P + TI |
| 5 | 4.5 | P + TS + I | P + I | P + TI |
| 6 | 5.0 | P + TS + I | P + I | P + TI |
| 7 | 7.0 | P + S + I | P + I | P + I |
| 8 | 7.5 | P + S + I | P + I | P + I |
| 9 | 8.0 | P + S + I | P + TI + I | P + I |

TABLE I-continued

| Flask | | DURATION | | |
| --- | --- | --- | --- | --- |
| No. | pH | 24 Hours | 48 Hours | 72 Hours |
| 10 | 8.5 | P + S + I | P + TS + I | P + I |
| 11 | 9.0 | P + S + I | P + TS + I | P + I |

TS: Trace Substrate
S: Substrate
TP: Trace Product
P: Product
I: Intermediate
TI: Trace Intermediate

EXAMPLE II

Preparation of Diol Intermediate

Reactions

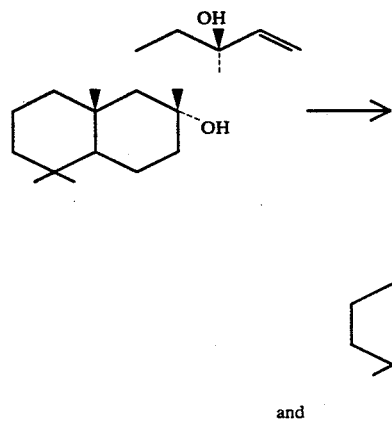

and

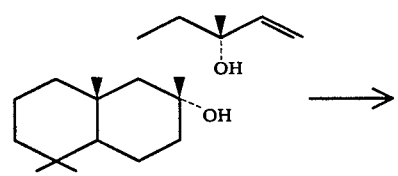

During screening of ten soil samples from Greenwood Forest, Barnegat Township, N.J., several flasks showed a spot on the TLC corresponding to the compound having the structure:

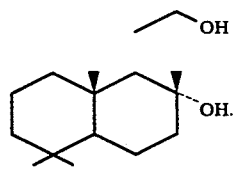

The following medium was prepared:

| NH₄NO₃ | 0.2% |
| --- | --- |
| KH₂PO₄ | 0.1% |
| MgSO₄.7H₂O | 0.05% |
| Yeast Extract | 0.2% |
| Dextrose | 1.0% |

Into a 500 ml flask was placed 100 ml medium and 1.0 g of a 50:50 mixture of sclareol powder:TWEEN ® 80. The flask was inoculated with 400 microliters of isolate of *Bensingtonia ciliata*, ATCC 20919. After one week at 25° C. and 150 rpm, the resulting product was extracted with 330 ml of ethyl acetate and the extract dried over anhydrous sodium sulfate. The solvent was removed on a rotary evaporator. The residue was dissolved in hot hexane and ethyl acetate. The resulting extract was permitted to evaporate for a period of 24 hours whereupon were obtained pure crystals (350 mg) of the compound having the structure:

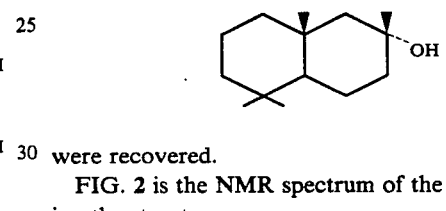

were recovered.

FIG. 2 is the NMR spectrum of the compound having the structure:

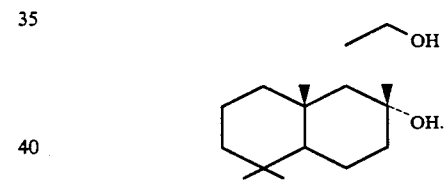

EXAMPLE III

Preparation of Sclareolide Using *Cryptococcus albidus* (Saito [Skinner var. albidus]), ATCC 20918

Reactions

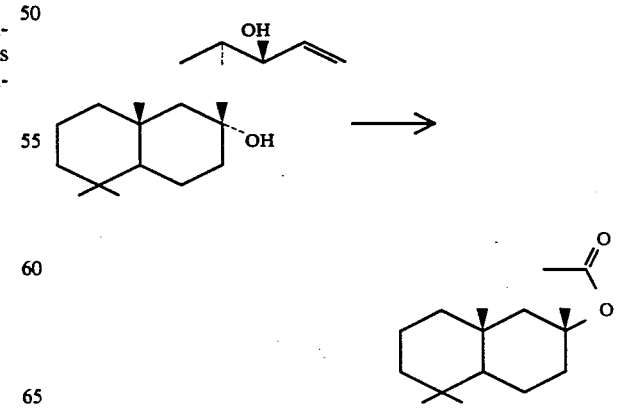

and

-continued

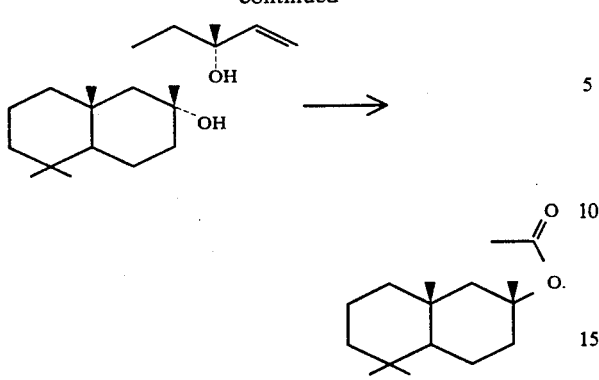

| MEDIUM | | FERMENTER PARAMETERS | |
|---|---|---|---|
| NH$_4$NO$_3$ | 0.2% | Temperature: | 25° C. |
| KH$_2$PO$_4$ | 0.1% | Aeration: | 1.0 l/min. |
| MgSO$_4$.7H$_2$O | 0.05% | Agitation: | 430 rpm |
| Yeast Extract | 0.2% | pH = 5.8 controlled with | |
| Antifoam | 10.0 g | 25% NaOH | |
| d-H$_2$O | 8.5 l | Duration: | 4 days |

SUBSTRATE PREPARATION

500 Grams of sclareol, 250 grams TWEEN ® 80 and 1125 grams of water were placed in a blender and mixed for 5 minutes to form an emulsion.

Fermenter containing above medium was sterilized at 121° C. for 30 minutes and cooled to 25° C. This fermenter was inoculated with 300 ml of 24 hour grown cells of *Cryptococcus albidus* (Saito [Skinner var. albidus]), ATCC 20918. 600 Grams of sclareol emulsion were added to time of inoculation and 600 g portions of emulsion were added at 24, 48, and 72 hours. At 96 hours, the contents of the fermenter were filtered through a 400 mesh sieve. The resulting crude solid product was dissolved in IPA, filtered and the solution concentrated to crystallize; 430 g of pure sclareolide were obtained.

FIG. 1 is a GC-MS spectrum for the initial reaction mass in this Example III. The peak indicated by reference numeral 21 is the peak for the sclareol which is a mixture (80:20) of the compounds having the structures:

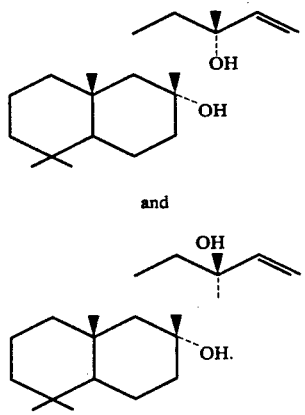

The peak indicated by reference numeral 20 is the peak for the internal standard, the compound having the structure:

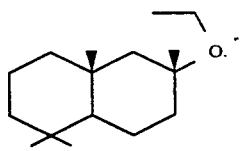

FIG. 3 is the NMR spectrum for the sclareolide produced according to this Example III having the structure:

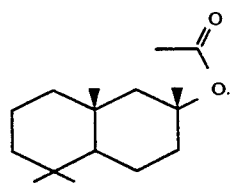

EXAMPLE IV

Production of Sclareolide from Sclareol Using *Cryptococcus albidus*, ATCC 20918

Same medium and parameters were used as in Example III. The mode of substrate preparation and addition were changed.

One hundred sixty grams of sclareol powder and 80 g of TWEEN ® 80 were added to the medium prior to sterilization.

Additional substrate was prepared by mixing finely ground sclareol (2 parts) and TWEEN ® 80 (1 part) to form a paste. Two hundred twenty five gram portions of this paste were added at 24, 48, and 72 hours after inoculation.

A total of 655 g of crude sclareolide having a purity of 67.34% was obtained.

EXAMPLE V

Preparation of Sclareolide from Sclareol Using *Cryptococcus albidus*, ATCC 20921

The same medium and parameters were used as in Example IV. The amount of substrate and agitation were changed.

One hundred fifty grams of sclareol and 75 grams of TWEEN ® 80 were added to the medium prior to sterilization.

Only 241 grams of substrate in paste form were added 24 hours after inoculation. Agitation was started at 430 rpm and later increased to 630 rpm.

A total of 491 g crude sclareolide having a purity of 44% was obtained, a 94.7% mole/mole conversion.

EXAMPLE VI

Preparation of Sclareolide from Sclareol, Diol Intermediate and Diol Acetate

Reaction

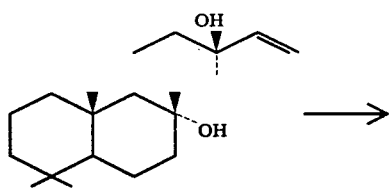

→

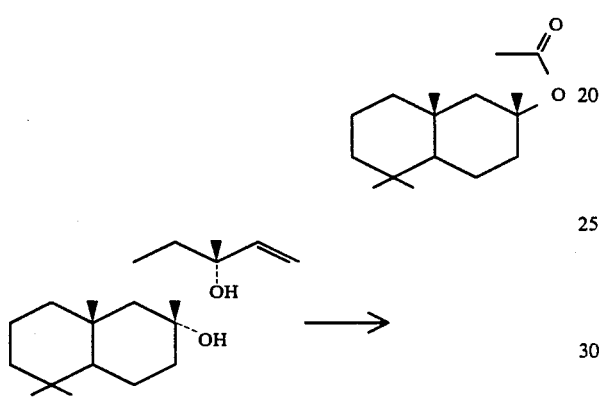

→

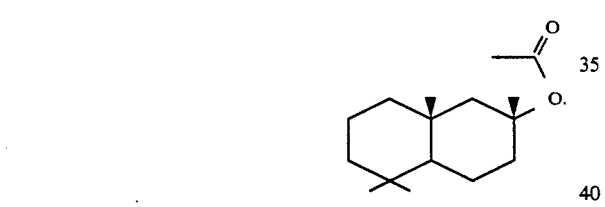

→ and

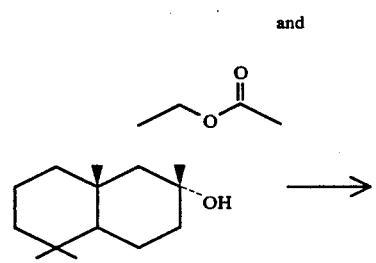

→

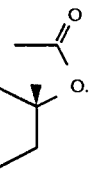

The following medium was prepared:

| | |
|---|---|
| NH$_4$NO$_3$ | 0.2% |
| KH$_2$PO$_4$ | 0.1% |
| MgSO$_4$.7H$_2$O | 0.05% |
| Yeast Extract | 0.2% |
| Dextrose | 0.5%. |

A 10 liter fermenter was used with the following operating conditions:

| | |
|---|---|
| Temperature | 25° C. |
| pH | 6.0 |
| Agitation | 430 rpm |
| Sterilization | 121° C. for 30 mins. |

The fermenter was inoculated with 100 ml of a 48 hour shake flask culture of *Cryptococcus albidus*, ATCC 20918 grown on the same medium at 25° C. and 150 rpm.

The course of fermentation is monitored using TLC based upon growth and substrate conversion, additional substrate is added. The following schedule is followed:

| Time | % of Fermenter Volume |
|---|---|
| 0 hrs. | 2.25% paste (1.5% sclareol) |
| 24 hrs. | 2.25% paste |
| 48 hrs. | 2.25% paste |
| 72 hrs. | 2.25% paste |
| 96 hrs. | Harvest. |

This schedule may be varied plus or minus 4 hours. The 0 hour substrate may be added before or after sterilization.

(i) The lactone product having the structure:

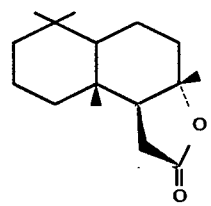

is a solid and may be recovered from the broth by one of the following methods:
(a) centrifigation at 10,000 rpm; or
(b) filtration (e.g., filter press).

(ii) The lactone product is purified by crystallization. The mother liquor is then concentrated to 25% of its original volume (via vacuum evaporation at 10 mm/Hg. pressure) and fractionated using silica gel column chromatography (Conditions: chromatographic column 1 foot in length×0.5" diameter). The first fraction is identified as the compound having the structure:

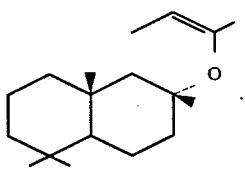

FIG. 4 is the NMR spectrum for the compound having the structure:

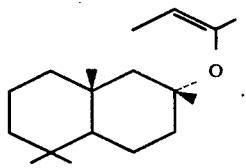

(iii) A portion of fermentation broth after filtration is acidified to a pH of 2 using aqueous one molar hydrochloric acid. The resultant slurry is then recentrifuged at 10,000 rpm. The resulting percipitate is further purified by crystallization and then fractionated using a silica gel chromatographic column (Conditions: 1 foot in length×0.5" in diameter). The fourth fraction in the eluate is the compound having the structure:

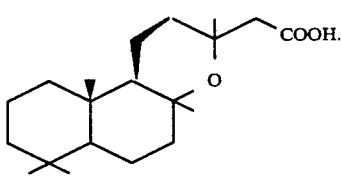

FIG. 5 is the NMR spectrum for the compound having the structure:

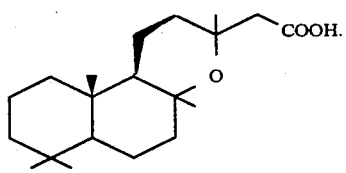

A tobacco blend is made up by mixing the following materials:

| Ingredients | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing "low delivery" cigarettes and the following formulation is compounded and incorporated into each of the cigarettes:

| Ingredients | Parts by Weight |
| --- | --- |
| Ethyl butyrate | 0.05 |

-continued

| Ingredients | Parts by Weight |
| --- | --- |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" "low delivery" cigarettes at the rate of 0.1%. One-third of these model cigarettes are treated in the tobacco section with the tricyclic ether-substituted acetic acid having the structure:

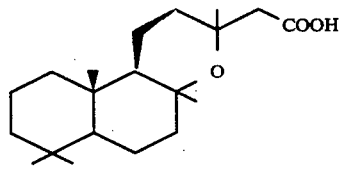

produced according to Example VI at a level of 25 ppm per cigarette.

Another one-third of these model cigarettes are treated in the filter with the tricyclic ether-substituted acetic acid having the structure:

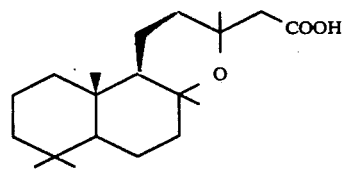

prepared according to Example VI at the rate of $2 \times 10^{-4}$ grams. When evaluated by paired comparison, the cigarettes treated both in the tobacco and in the filter with the tricyclic ether-substituted acetic acid of our invention having the structure:

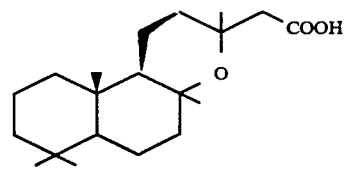

produce according to Example VI are found in smoke flavor, to be more tobacco-like, and to be richer, smoother and have more tobacco body in the model cigarette not containing the tricyclic ether-substituted acetic acid of our invention having the structure:

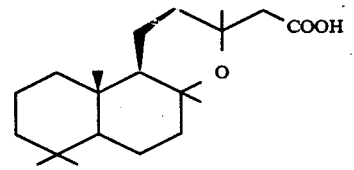

Prior to smoking, the tobacco composition has a woody and citrusy aroma profile with a strong smooth tobacco body when the composition contains the tricyclic ether-substituted acetic acid of our invention having the structure:

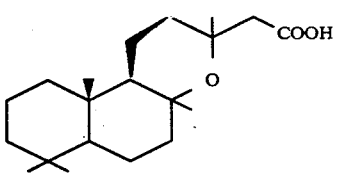

and does not have such smooth tobacco body without the tricyclic ether-substituted acetic acid of our invention having the structure:

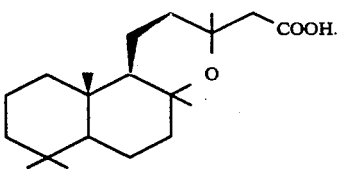

The rich, smooth "high body" character in the smoke flavor is imparted in both the main stream and in the side stream on smoking when using the tricyclic ether-substituted acetic acid of our invention having the structure:

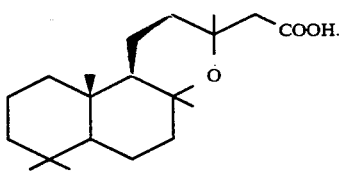

What is claimed is:

1. A process for augmenting or enhancing the aroma or taste of a consumable material selected from the group consisting of smoking tobacco compositions and smoking tobacco articles comprising the step of adding to said consumable material an aroma or taste imparting, augmenting or enhancing quantity of the tricyclic ether-substituted acetic acid having the structure:

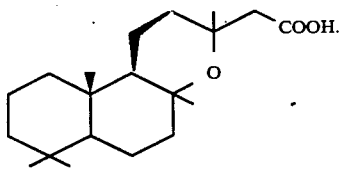

2. A smoking tobacco composition comprising smoking tobacco and intimately admixed therewith, an aroma or taste augmenting, enhancing or imparting quantity of a tricyclic ether-substituted acetic acid having the structure:

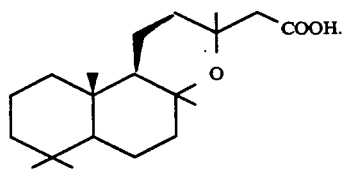

3. A smoking tobacco article comprising a cylindrical body of smoking tobacco having a longitudinal circumferential section and two opposing ends, said body of tobacco being surrounded on said longitudinal circumferential section by a wrapper and having a filter at one end thereof, and intimately admixed with said filter, contained in said tobacco body or coated on said wrapper, an aroma or taste augmenting, enhancing or imparting quantity of a tricyclic ether-substituted acetic acid having the structure:

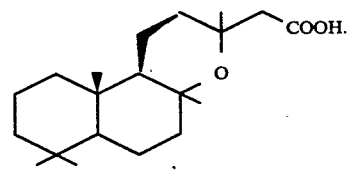

* * * * *